United States Patent [19]

Maegawa et al.

[11] 4,297,508

[45] Oct. 27, 1981

[54] PROCESS FOR PRODUCING 2 HYDROXY-NAPHTHALENE-3-CARBOXYLIC ACID

[75] Inventors: Yuzo Maegawa, Oita; Fujio Masuko, Oita; Makoto Nakamura, Ibaraki, all of Japan

[73] Assignee: Sumitomo Chemical Company, Limited, Osaka, Japan

[21] Appl. No.: 218,973

[22] Filed: Dec. 22, 1980

[30] Foreign Application Priority Data

Dec. 25, 1979 [JP] Japan .................................. 54-170056
Sep. 22, 1980 [JP] Japan .................................. 55-132033

[51] Int. Cl.³ ............................................. C07C 51/15
[52] U.S. Cl. .................................................. 562/425
[58] Field of Search .......................................... 562/425

[56] References Cited

U.S. PATENT DOCUMENTS 4,020,102  4/1977  Seeger et al. ...................... 562/425
4,038,309  7/1977  Hoch et al. ......................... 562/425
4,239,913  12/1980 Ueno et al. ......................... 562/425

Primary Examiner—Alan Siegel
Attorney, Agent, or Firm—Sughrue, Mion, Zinn, Macpeak and Seas

[57] ABSTRACT

A process for producing 2-hydroxynaphthalene-3-carboxylic acid comprising reacting carbon dioxide with a homogeneous liquid mixture comprising an alkali metal salt of β-naphthol, β-naphthol and a specific alkylbenzene is disclosed.

14 Claims, 1 Drawing Figure

PROCESS FOR PRODUCING 2 HYDROXY-NAPHTHALENE-3-CARBOXYLIC ACID

FIELD OF THE INVENTION

This invention relates to an improved process for producing 2-hydroxynaphthalene-3-carboxylic acid.

BACKGROUND OF THE INVENTION

2-Hydroxynaphthalene-3-carboxylic acid is a compound important as an intermediate for various dyes and pigments, especially for the coupling component (grounder) of azoic dyes and the coupling component of azo dyes and azo lakes. The production of dyes and pigments of good quality require pure 2-hydroxynaphthalene-3-carboxylic acid that contains no impurities, particularly β-naphthol or tar-like by-product.

The traditional process for the production of 2-hydroxynaphthalene-3-carboxylic acid uses the Kolbe-Schmitt reaction which is a solid-gas phase reaction between an alkali metal salt of β-naphthol and carbon dioxide (*Ullmanns Encyklopadie der Technischen Chemie*, vol. 12, p. 606). However, the Kolbe-Schmitt reaction is difficult to control and constant yield is hard to achieve: the reaction involves great loss of β-naphthol because it is a thermally heterogeneous reaction: the reaction takes place at least 40 to 50 hours to complete dehydration for salt formation and carboxylation: and for another, to prevent incomplete dehydration that results in the absence of carboxylation, a preliminary treatment under vacuum is necessary.

German Pat. No. 423034 describes an improved method wherein an alkali metal salt of β-naphthol is reacted with carbon dioxide under pressure in the presence of excess β-naphthol. The method is still unsatisfactory because β-naphthol formed as an azeotropic product solidifies during dehydration, the yield of the end product is only about 70%, and the reaction requires a pressure as high as 40 to 100 kg/cm² G.

Japanese Patent Application (OPI) Nos. 79256/79 and 79257/79 (the term "OPI" as used herein means an unexamined published Japanese Patent Application) describe another improved method wherein a liquid mixture comprising an alkali salt of β-naphthol, β-naphthol and gas oil or kerosine is reacted with carbon dioxide. The method also has several defects: dehydration is difficult to achieve in the heterogeneous liquid mixture that easily separates into two phases; a good suspension is particularly difficult to form in continuous reaction; and an additional apparatus is necessary to remove the excess solvent by separation.

Japanese Patent Application (OPI) No. 1723/72 proposes the use of diphenyl, diphenyl ether, or an alkyl naphthalene as the reaction solvent. The proposal is interesting in that the reaction with carbon dioxide is performed in a solution state, but it still has several defects: the solvent is expensive, it is either high-melting or low-boiling, and it has an unpleasant smell; and rapid dehydration is difficult.

As a result of various studies to eliminate the defects of the conventional techniques, it has been found that an object of the present invention can be achieved by first forming a homogeneous solution of an akali metal salt of β-naphthol using β-naphthol and an alkylbenzene of the formula (I) which is defined below and then reacting the solution with carbon dioxide.

SUMMARY OF THE INVENTION

An object of this invention is to provide a process for producing 2-hydroxynaphthalene-3-carboxylic acid comprising reacting carbon dioxide with a homogeneous liquid mixture comprising an alkali metal salt of β-naphthol, β-naphthol and an alkylbenzene of the formula (I):

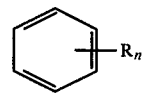
(I)

wherein R is the same or different and is a straight or branched alkyl group having 1 to 4 carbon atoms; and n is an integer of 1 to 6.

According to this invention, 2-hydroxynaphthalene-3-carboxylic acid of high purity can be produced continuously in high yield, requiring a considerably reduced period of dehydration, salt formation, and reaction between carbon dioxide and the liquid mixture of the alkali metal salt of β-naphthol, β-naphthol and alkyl benzene. Since the process involves a homogeneous system, no β-naphthol loss due to thermally heterogeneous reaction occurs.

DETAILED DESCRIPTION OF THE INVENTION

Figure 1:
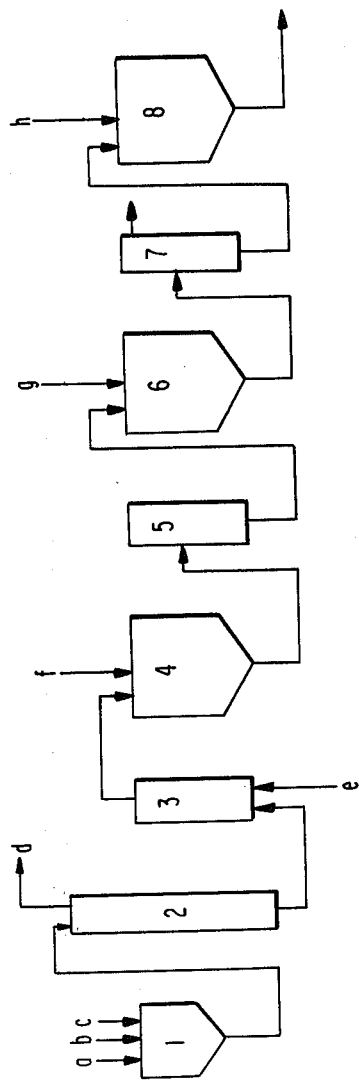
FIG. 1 is a flow chart showing one embodiment of the process of this invention.

All compounds of the formula (I) can be used as the alkylbenzene in this invention. Illustrative alkylbenzenes include propylbenzene, butylbenzene, isopropylbenzene, t-butylbenzene, ethyltoluene, diethyltoluene, isopropyltoluene, diisopropyltoluene, butyltoluene, t-butyltoluene, propylbutyltoluene, dibutyltoluene, trimethylbenzene, tripropylbenzene, triisopropylbenzene, tributylbenzene, tri-t-butylbenzene, triethyltoluene, tripropyltoluene, triisopropyltoluene, tributyltoluene, tri-t-butyltoluene, tetramethylbenzene, pentamethylbenzene, hexamethylbenzene, tetraethylbenzene, pentaethylbenzene, hexaethylbenzene, tetrapropylbenzene, diisopropylbenzene, and mixtures thereof. Particularly preferred alkylbenzenes are those compounds which are represented by the formula (II):

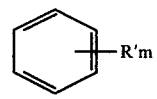
(II)

wherein R' is the same or different and is a straight or branched alkyl group having 1 to 3 carbon atoms; and m is an integer of 3 or 4.

Examples of R' in the formula (II) are a methyl group, an ethyl group, a propyl group and an isopropyl group. Specific examples of the preferred alkylbenzene are triethylbenzene, triisopropylbenzene and diisopropyltoluene which may be a mixture of their isomers.

The alkali metal salt of β-naphthol used in this invention includes sodium, potassium and lithium salts of β-naphthol. A mixture of these salts may be used. A sodium salt of β-naphthol is preferred in industrial applications.

One illustrative embodiment of the process of this invention is described hereunder.

A homogeneous liquid mixture of an alkali metal salt of β-naphthol, β-naphthol and an alkylbenzene is preferably prepared simultaneously with the reaction for the formation of the alkali metal salt of β-naphthol and removal of water produced by that reaction. For this purpose, to a solution of β-naphthol in an alkylbenzene is added an alkali metal salt forming agent such as an alkali metal hydroxide (preferably sodium hydroxide) in an amount less than an equivalent amount with respect to β-naphthol so as to provide a desired amount of an alkali metal salt, and reaction is performed under fractional dehydration conditions. Preferably, an inert gas such as nitrogen is supplied to the reaction system. If the reaction mixture obtained does not have the intended formulation, adjustment may be made by adding or removing a suitable amount of an alkylbenzene or β-naphthol.

The above procedure provides a transparent, homogeneous liquid reaction mixture which preferably comprises one mol of an alkali metal salt of β-naphthol, 0.1 to 5 mols, preferably 0.3 to 2 mols, of β-naphthol, and an alkylbenzene in an amount of 0.1 to 5 times, preferably 0.2 to 2 times, the weight of the alkali metal salt of β-naphthol.

It is with particular advantage to shorten the period of dehydration using a fractionating column means. In one embodiment, a fractionating column is fed with a mixture of β-naphthol, an alkylbenzene and an alkali metal salt forming agent in an amount less than an equivalent amount with respect to β-naphthol so as to provide a desired amount of an alkali metal salt. To prevent the clogging of the column due to a crystal deposit, the molar ratio of the alkali metal forming agent to β-naphthol is preferably between about 0.45:1 and 0.63:1, more preferably between about 0.50:1 and 0.59:1, and the weight ratio of the alkylbenzene to β-naphthol is preferably between 0.1:1 and 0.8:1, more preferably between 0.3:1 and 0.8:1. When the molar ratio of β-naphthol to the alkali metal salt of β-naphthol is small, the amount of the alkylbenzene used is also preferably reduced, and if its molar ratio is great, the amount of the alkylbenzene is preferably increased. The dehydration in the fractionating column is usually performed at 100° to 240° C. to remove water as an overhead distillate. By so doing, a water-free, homogeneous liquid mixture can be produced continuously without clogging the fractionating column wherein the salt formation and dehydration take place. Continuous dehydration achieves simpler process control than batch process and only about one hour is required for dehydration while 4 to 5 hours are required in the conventional process, so the thermal deterioration of β-naphthol which has been in the range of from 0.5 to 1.0% is reduced to the range of from about 0.1 to 0.2% in this invention. It has also been found that the process of this invention can reduce the content of water detrimental to carboxylation to about 50 ppm or less. Another advantage of this invention is that the use of the homogeneous liquid mixture thus obtained permits easy and continuous reaction with carbon dioxide in the subsequent step.

The success of dehydration in a fractionating column is based on the finding of the conditions necessary for a homogeneous liquid mixture of an alkali metal salt of β-naphthol, β-naphthol and a mixture of diisopropyltoluene isomers (as a compound of the formula (I)) to remain liquid throughout the period of dehydration. Part of the data obtained during review of these conditions is set forth in Table 1 below.

TABLE 1

| Molar Ratio of β-naphthol/ Sodium β-naphtholate | Temperature at which Crystallization Occurred During Dehydration |
|---|---|
| 0.56:1 | 160 to 215° C. |
| 0.67:1 | 198 to 205° C. |
| 0.82:1 | no crystallization at 100 to 230° C. |
| 1.00:1 | no crystallization at 100 to 230° C. |
| 1.25:1 | no crystallization at 100 to 230° C. |

[Note]
The weight ratio of diisopropyltoluene to sodium β-naphtholate was in the range of from 0.6:1 to 0.8:1.

The homogeneous liquid mixture thus obtained is reacted with carbon dioxide at a temperature of 200° C. or higher, preferably between 230° and 300° C., more preferably between 240° and 280° C., at a $CO_2$ pressure of 20 kg/cm² G or less, preferably between 1 and 15 kg/cm² G, more preferably between 3 and 8 kg/cm² G. The reaction generally continues for 0.5 to 5 hours, preferably from 0.5 to 3 hours.

After the reaction, 2-hydroxynaphthalene-3-carboxylic acid can be isolated from the reaction mixture by a conventional method. A preferred method is as follows: under cooling, water or a mixture of water and an extraction solvent is added to the reaction mixture, and at a controlled temperature between 80° and 90° C., a mineral acid or an aqueous solution thereof is added to the mixture to adjust its pH to between 4 and 8, preferably between 5 and 7, more preferably between 5.5 and 6.5, at which point the mixture is then separated into an organic layer comprising the alkylbenzene, β-naphthol and a tar-like substance and an aqueous layer containing a water-soluble salt of 2-hydroxynaphthalene-3-carboxylic acid and other substances. The separation is performed at 40° to 100° C., preferably 75° to 95° C., and more preferably 80° to 90° C. To the aqueous layer is added an extraction solvent in an amount of 0.3 to 2.0 times, preferably 0.3 to 1.0 time, the weight of the aqueous layer to extract the β-naphthol again at 40° to 100° C., preferably at 50° to 90° C., followed by separation of the aqueous layer which is adjusted with a mineral acid such as sulfuric acid to a pH of 1 to 3, preferably 1.5 and 2, and the resulting precipitate is filtered and dried to give a high yield of 2-hydroxynaphthalene-3-carboxylic acid.

From the organic layer that is separated from the reaction mixture by addition of water, neutralization and separation, the alkylbenzene and β-naphthol are recovered by distillation. Alternatively, β-naphthol is obtained as sodium β-naphtholate by back extraction with an aqueous alkali solution and the solvent is recovered by distillation. The organic layer separated by the second extraction may be directly freed of the extraction solvent and β-naphthol by distillation. Alternatively, β-naphthol is obtained as sodium β-naphtholate by back extraction with an aqueous alkali solution and the solvent is recycled to the extraction step either directly or after purification by distillation.

The solvent used for the extraction in the process of this invention is either an alkylbenzene the same as those employed in the preparation of the homogeneous liquid mixture or it may be a benzene compound such as xylene, toluene, chlorobenzene, dichlorobenzene or benzene. Preferred solvents are xylene and toluene.

This invention can be performed as a continuous process that comprises the steps of carboxylation, extraction, separation, precipitation with acid, and filtration as well as alkali metal salt formation and dehydration. In a particularly advantageous embodiment, the steps of salt formation and dehydration are achieved continuously in a fractionating column means, and the subsequent steps of carboxylation, extraction, separation, precipitation with acid and filtration are also performed continuously, and one of such preferred embodiment is schematically represented in the flow chart of FIG. 1, wherein 1 is an ingredients mixing tank, 2 is a salt formation/dehydration column, 3 is a carboxylation tank, 4 is a water addition tank, 5 and 7 are separation tanks, 6 is an extraction tank, and 8 is a tank in which to precipitate with acid, a is β-naphthol, b is a reaction solvent (diisopropyltoluene), c is an alkali metal salt forming agent (aqueous sodium hydroxide solution), d is water, e is carbon dioxide, f and h are mineral acids, and g is an extraction solvent (xylene).

The process of this invention is described in greater detail by reference to the following examples which are given here for illustrative purposes only and are by no means intended to limit the scope of the invention.

EXAMPLE 1

A 30-liter reactor was charged continuously with 75 kg/hr of β-naphthol, 30 kg/hr of diisopropyltoluene (isomer mixture) and 23.5 kg/hr of 50% aqueous sodium hydroxide solution while it was held at 100° C. in a nitrogen atmosphere. The liquid mixture was fed to a fractionating column while water was withdrawn as an overhead distillate. During fractionation, the reboiler was kept between 230° and 240° C. The residence time in the column was about 20 minutes and the distillate withdrawal rate was 51.1 kg/hr. The residue from the column was supplied continuously to an autoclave with a metering pump under pressure at a rate of 111.46 kg/hr for reaction with carbon dioxide. The reaction conditions were as follows: a temperature of 260° C., a total pressure of 7.0 kg/cm$^2$ G, and a residence time of 1.0 hr. The reaction mass was recovered from the reactor at a rate of 117.0 kg/hr and supplied to a water addition tank where it was mixed with 250 kg/hr of water and the pH of the mixture was adjusted to 6.0 with 70% sulfuric acid at a controlled temperature of 90° C. The mixture was supplied to a separation tank where it was separated into the organic layer and the aqueous layer. The aqueous layer was fed to an extraction tank where β-naphthol in the aqueous layer was extracted with 85 kg/hr of xylene. The extraction conditions were as follows: an extraction temperature of 80° to 85° C., an agitation period of 10 minutes, a standing period of 10 minutes, and a pH of 6.0 (adjusted with dilute sulfuric acid). The mixture was then supplied to a separation tank where it was separated into the organic layer and the aqueous layer. The aqueous layer was sent to a precipitation tank where it was adjusted to a pH of 2.0 with 70% sulfuric acid at 80° C. The precipitate was filtered at 80° C. to give 24 kg/hr of 2-hydroxynaphthalene-3-carboxylic acid (99% purity and β-naphthol content of 0.05%). The yield of 2-hydroxynaphthalene-3-carboxylic acid was 43.5% based on the sodium β-naphtholate and was 86% based on β-naphthol consumed. The recovery rate of β-naphthol was 54 kg/hr.

EXAMPLE 2

A reactor was charged continuously with 50 kg/hr of β-naphthol, 20 kg/hr of diisopropyltoluene (isomer mixture) and 13.9 kg/hr of 50% aqueous sodium hydroxide solution while it was held at 100° C. in a nitrogen atmosphere. The mixture was fed to a fractionating column at a rate of 83.9 kg/hr while water was withdrawn as an overhead distillate at a rate of 10.1 kg/hr. During the fractionation, the reboiler was held at 230° C. The residue from the column was supplied continuously to an autoclave with a metering pump under pressure at a rate of 73.8 kg/hr for reaction with carbon dioxide. The reaction conditions were as follows: a temperature of 260° C., a total pressure of 7.0 kg/cm$^2$ G, and a residence time of 1.5 hr. The reaction mass was recovered from the autoclave at a rate of 77.1 kg/hr and supplied to a water addition tank where it was mixed with 165 kg/hr of water, and the mixture was treated with sulfuric acid to adjust its pH to 6.0 at a controlled temperature between 85° and 90° C. The mixture was supplied to a separation tank where it was separated into the organic layer and the aqueous layer. The aqueous layer was fed to an extraction tank where β-naphthol was extracted with 60 kg/hr of toluene. The extraction temperature was between 80° and 85° C. The mixture was then supplied to a separation tank where it was separated into the organic layer and the aqueous layer. The aqueous layer was sent to an acid precipitation tank where it was adjusted to a pH of 2.0 with sulfuric acid at 80° C. The precipitate was filtered to give 14.4 kg/hr of 2-hydroxynaphthalene-3-carboxylic acid (99% purity and β-naphthol content less than 0.1%). The yield of 2-hydroxynaphthalene-3-carboxylic acid was 44% on the basis of the sodium β-naphtholate and was 85% on the basis of β-naphthol consumed.

EXAMPLE 3

A pressure reactor was charged with 750 g of β-naphthol, 300 g of diisopropyltoluene and 135 g of sodium hydroxide and the reaction was performed under the azeotropic condition in a nitrogen atmosphere with stirring. The resulting water was distilled off as a mixture with diisopropyltoluene. The distillate was separated into water and diisopropyltoluene, and only the diisopropyltoluene layer was returned to the reactor. A transparent, homogeneous liquid mixture comprising a sodium salt of β-naphthol, β-naphthol and diisopropyltoluene was produced. The mixture was reacted with carbon dioxide at 260° C. for 2 hours at a $CO_2$ pressure of 5 kg/cm$^2$ G.

Then, the reaction mixture was mixed with 1000 g of water and 3000 g of diisopropyltoluene. The mixture was adjusted to a pH of 6.0 with 70% sulfuric acid at a controlled temperature of 90° C. and separated into the aqueous layer and the diisopropyltoluene layer at 90° C. To the aqueous layer was added 3000 g of diisopropyltoluene for another extraction at 90° C., followed by phase separation at 90° C. The pH of the aqueous layer was adjusted to 2.0 with 70% sulfuric acid at 85° C., and the resulting precipitate was filtered at 85° C. to give 280 g of 2-hydroxynaphthalene-3-carboxylic acid (99.0% purity and β-naphthol content of 0.1%). The yield of 2-hydroxynaphthalene-3-carboxylic acid was 44% on the basis of the sodium salt of β-naphthol and was 87% on the basis of β-naphthol consumed. The amount of β-naphthol recovered was 503 g.

EXAMPLE 4

A mixture of a sodium salt of β-naphthol, β-naphthol and diisopropyltoluene was reacted with carbon dioxide in the same manner as in Example 3, and to the reaction mixture were added 1000 g of water and 3060 g of diisopropyltoluene obtained in the secondary extraction of Example 3. The pH of the mixture was adjusted to 6.0 with 70% sulfuric acid at a controlled temperature of 90° C. Then, the mixture was separated into the aqueous layer and the diisopropyltoluene layer at 90° C.

The diisopropyltoluene layer was extracted with 270 g of a 50% aqueous sodium hydroxide solution and the aqueous sodium hydroxide solution layer was separated from the diisopropyltoluene layer at 90° C. The aqueous sodium hydroxide solution layer was then mixed with 248 g of β-naphthol and 300 g of diisopropyltoluene and the mixture was subjected to dehydration with heat under stirring. Then, in the same manner as in Example 3, the mixture was reacted with carbon dioxide, the reaction product was subjected to two cycles of extraction and phase separation, and the aqueous layer was subjected to precipitation with acid to give 278 g of 2-hydroxynaphthalene-3-carboxylic acid. The yield of 2-hydroxynaphthalene-3-carboxylic acid was 43.8% based on the sodium salt of β-naphthol and 86% based on β-naphthol consumed. The amount of β-naphthol recovered was 502 g.

EXAMPLE 5

A homogeneous liquid mixture was prepared in the same manner as in Example 3 except that diisopropyltoluene was replaced by 300 g of cymene. The mixture was then reacted with carbon dioxide at 250° C. for 2 hours at a $CO_2$ pressure of 7 kg/cm² G. The reaction product was worked up as in Example 3 except that diisopropyltoluene was replaced by cymene; 254 g of 2-hydroxynaphthalene-3-carboxylic acid (99% purity and β-naphthol content of 0.1%) was produced. The yield of 2-hydroxynaphthalene-3-carboxylic acid was 40% based on the sodium salt of β-naphthol and 85% based on β-naphthol consumed. The amount of β-naphthol recovered was 521 g.

EXAMPLE 6

A homogeneous liquid mixture was prepared in the same manner as in Example 3 except that diisopropyltoluene was replaced by 300 g of diethylbenzene. The mixture was then reacted with carbon dioxide at 250° C. for 2.5 hours at a $CO_2$ pressure of 5 kg/cm² G. The reaction product was worked up as in Example 3 except that diisopropyltoluene was replaced by diethylbenzene; 270 g of 2-hydroxynaphthalene-3-carboxylic acid (99% purity and β-naphthol content of 0.1%) was obtained. The yield of 2-hydroxynaphthalene-3-carboxylic acid was 43% based on the sodium salt of β-naphthol and 86% based on β-naphthol consumed. The amount of β-naphthol recovered was 510 g.

EXAMPLE 7

A reactor was charged with 75 kg/hr of β-naphthol, 30 kg/hr of diisopropyltoluene and 30 kg/hr of a 45% aqueous sodium hydroxide solution for performing the formation of an alkali metal salt of β-naphthol and primary dehydration in a nitrogen atmosphere at 180° C. (residence time: 2 hr). The reaction mixture was fed to the second reactor at a rate of 119 kg/hr where it was subjected to reaction for the formation of an alkali metal salt of β-naphthol and secondary dehydration in a nitrogen atmosphere at 230° C. (residence time: 1 hr). A homogeneous liquid mixture (salt mass) in the second reactor was sent to a carboxylation reactor at a rate of 112 kg per hour where it was reacted with carbon dioxide at 260° C. at a $CO_2$ pressure of 5 kg/cm² G (residence time: 2 hr). The reaction mixture was cooled through a heat exchanger and sent to a primary extraction tank where it was mixed with 200 l/hr of water, 306 kg/hr of diisopropyltoluene layer from a secondary extraction tank and 70% sulfuric acid to adjust its pH to 6.0 at a controlled temperature of 90° C. (residence time: 0.5 hr). The mixture was sent to a separation tank where it was separated into the diisopropyltoluene layer and the aqueous layer at 90° C. The upper diisopropyltoluene layer was freed of β-naphthol by a recovery device. The lower aqueous layer was supplied to the secondary extraction tank where it was mixed with 300 kg of diisopropyltoluene per hour at 90° C. (residence time: 0.5 hr). The mixture was then supplied to a separation tank where it was separated into the diisopropyltoluene layer and the aqueous layer at 85° C. The upper diisopropyltoluene layer was returned to the primary extraction tank and the lower aqueous layer was transferred to an acid precipitation tank where it was adjusted to a pH of 2.0 with dilute sulfuric acid at 85° C. The resulting precipitate was filtered under heat at 85° C. to give 27.8 kg/hr of 2-hydroxynaphthalene-3-carboxylic acid (99% purity and β-naphthol content of 0.1%). The yield of 2-hydroxynaphthalene-3-carboxylic acid was 43.8% based on the sodium salt of β-naphthol and 88.5% based on β-naphthol consumed. The β-naphthol recovered was 50.9 kg per hour.

While the invention has been described in detail and with reference to specific embodiments thereof, it will be apparent to one skilled in the art that various changes and modifications can be made therein without departing from the spirit and scope thereof.

What is claimed is:

1. A process for producing 2-hydroxynaphthalene-3-carboxylic acid comprising reacting carbon dioxide with a homogeneous liquid mixture comprising an alkali metal salt of β-naphthol, β-naphthol and an alkylbenzene of the formula (I):

(I)

wherein R is the same or different and is a straight or branched alkyl group having 1 to 4 carbon atoms and n is an integer of 1 to 6.

2. A process according to claim 1, wherein the formula (I) is the formula (II):

(II)

wherein R' is the same or different and is a straight or branched alkyl group having 1 to 3 carbon atoms and m is an integer of 3 or 4.

3. A process according to claim 1, wherein the alkylbenzene of the formula (I) is diisopropyltoluene.

4. A process according to claim 1, wherein the molar ratio of the β-naphthol to the alkali metal salt of β-naphthol in the homogeneous liquid mixture is between 0.1:1 and 5:1 and the weight ratio of the alkylbenzene to the alkali metal salt of β-naphthol is between 0.1:1 and 5:1, respectively.

5. A process according to claim 1, wherein the molar ratio of the β-naphthol to the alkali metal salt of β-naphthol in the homogeneous liquid mixture is between 0.6:1 and 1.25:1 and the weight ratio of the alkylbenzene to the alkali metal salt of β-naphthol is between 0.1:1 and 1.0:1, respectively.

6. A process according to claim 1, wherein the preparation of the homogeneous liquid mixture is simultaneous with the formation of an alkali metal salt of β-naphthol and dehydration.

7. A process according to claim 6, wherein the preparation of the homogeneous liquid mixture involves dehydration in a fractionating column means.

8. A process according to claim 6 or 7, wherein the dehydration is performed at a temperature between 100° and 240° C.

9. A process according to claim 1, wherein the homogeneous liquid mixture is reacted with carbon dioxide at a temperature higher than 200° C.

10. A process according to claim 1, wherein the homogeneous liquid mixture is reacted with carbon dioxide at a $CO_2$ pressure less than 20 kg/cm$^2$ G.

11. A process according to claim 1 or 6, wherein (1) the reaction product is mixed with water or a mixture of water and an extraction solvent, followed by neutralization, extraction and separation into the aqueous layer and the organic layer, (2) the aqueous layer is subjected to extraction with an extraction solvent, followed by separation into the aqueous layer and the organic layer, and (3) the aqueous layer is treated with an acid to isolate 2-hydroxynaphthalene-3-carboxylic acid as a precipitate.

12. A process according to claim 11, wherein the extraction solvent is the same as what is used in the carboxylation.

13. A process according to claim 11, wherein the extraction solvent is a benzene compound that differs from the solvent used in the carboxylation.

14. A process according to claim 11, wherein the formation of the alkali metal salt of β-naphthol, dehydration, carboxylation, extraction and precipitation with an acid are performed continuously.

* * * * *